United States Patent [19]
Farrington

[11] Patent Number: 6,116,078
[45] Date of Patent: Sep. 12, 2000

[54] ADJUSTABLE FIXTURE FOR HEAD IMPACT TESTING

[75] Inventor: Stephen D. Farrington, Kingston, N.H.

[73] Assignee: Textron Automotive Company, Inc., Troy, Mich.

[21] Appl. No.: 09/327,881

[22] Filed: Jun. 8, 1999

[51] Int. Cl.[7] .................................................. G01M 7/00
[52] U.S. Cl. ........................................... 73/12.09; 73/866
[58] Field of Search .............................. 73/12.01, 12.04, 73/12.07, 12.09, 866

[56] References Cited

U.S. PATENT DOCUMENTS

| | | |
|---|---|---|
| 3,373,716 | 3/1968 | Williams . |
| 3,927,554 | 12/1975 | Langhorst . |
| 3,974,313 | 8/1976 | James ...................................... 428/176 |
| 4,161,874 | 7/1979 | Specker et al. . |
| 4,275,912 | 6/1981 | Bayer ...................................... 293/120 |
| 4,545,236 | 10/1985 | Turczyn . |
| 4,691,556 | 9/1987 | Mellander et al. . |
| 4,721,329 | 1/1988 | Brantman et al. ...................... 280/751 |
| 5,468,045 | 11/1995 | Weber ................................ 297/216.11 |
| 5,483,845 | 1/1996 | Stein et al. . |

*Primary Examiner*—Max Noori
*Attorney, Agent, or Firm*—Reising, Ethington, Barnes, Kisselle, Learman & McCulloch, P.C.

[57] ABSTRACT

An adjustable impact test fixture (10) for testing impact characteristics of interior trim panels (22). The fixture (10) comprises a support (12), a backing plate (14) attached to the support, and a movable floating plate (16) supported in spaced-apart relation to the backing plate. The fixture further includes one or more energy absorbing inserts (18) that are removably disposed between the backing plate (14) and the floating plate (16). Each insert (18) causes the fixture (10) to have a predetermined or known impact characteristic. The fixture (10) further includes a mounting assembly (20) adapted to fixedly secure a trim panel portion (22) to the floating plate (16). A corresponding method includes the steps of: determining an impact characteristic associated with a given energy absorbing insert; inserting the insert between a support and a floating plate; mounting a vehicle trim panel on the floating plate; causing a test object to impact the trim panel portion; determining at least one characteristic of the impact; and comparing the characteristic with a reference characteristic.

11 Claims, 2 Drawing Sheets

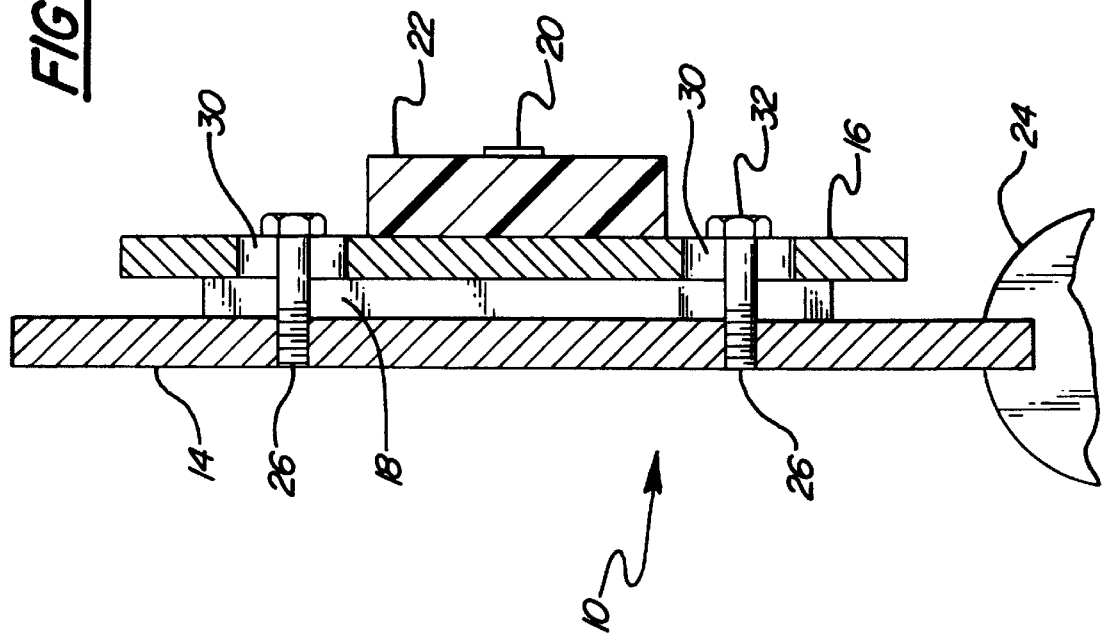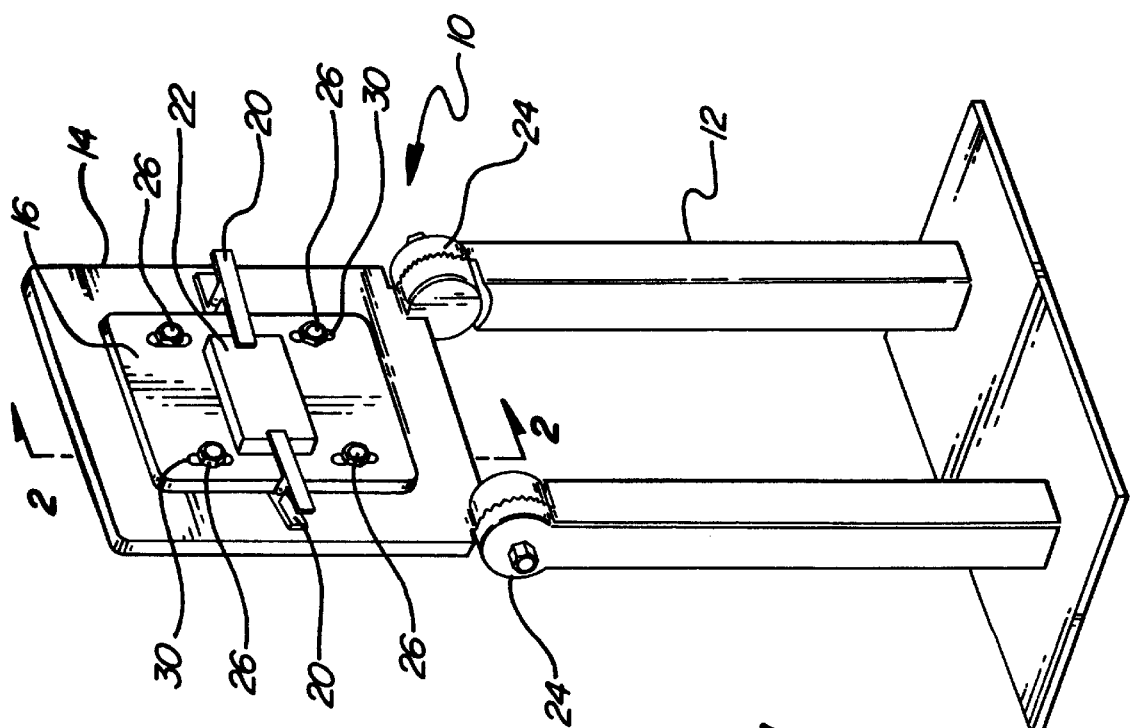

ADJUSTABLE FIXTURE FOR HEAD IMPACT TESTING

TECHNICAL FIELD

The subject invention relates to impact testing, and specifically to a method and fixture for impact testing of interior trim components of a vehicle.

BACKGROUND OF THE INVENTION

Manufacturers of vehicle interior trim products need to meet certain safety standards for impact characteristics of the products. Some of the standards are imposed by the industry; others are imposed by various governmental agencies. For example, manufacturers engineer trim products that do not exceed certain head impact criteria ("HIC") values.

In order to meet the standards, manufacturers perform impact tests on representative products to ensure that the products conform. In some cases, the manufacturers have tested the products with set-ups that closely resemble the interior of a vehicle. This is not necessary and it adds a great deal of cost because at least portions of the set-ups, including sheet metal, may be damaged or destroyed in the testing.

Some companies have devised a simpler reusable fixture that allows for acceptable testing without the need to damage or destroy a set-up. It is believed that Dow, for example, uses a fixture having a support, a fixed plate mounted to the support, and a floating plate mounted to the fixed plate. This fixture also includes a spring or a fluid-type shock absorber fixedly disposed between the fixed plate and the floating plate. It is believed that the spring or shock absorber can be adjusted or calibrated so the test fixture can simulate different known impact characteristics (e.g. relating to soft or hard surfaces). However, this adjustment or calibration takes time and might involve a degree of error.

SUMMARY OF THE INVENTION AND ADVANTAGES

The improved adjustable fixture comprises a support, a backing plate attached to the support, and a movable or floating plate supported in spaced-apart relation to the backing plate. The fixture further includes one or more energy absorbing inserts that are removably disposed between the backing plate and the floating plate. Each insert causes the fixture to have a predetermined or known impact characteristic. The fixture further includes a mounting assembly adapted to fixedly secure a trim panel to the floating plate.

The system involves a corresponding method including the steps of: determining an impact characteristic associated with a given energy absorbing insert; inserting the insert between a support and a floating plate; mounting a vehicle trim panel on the floating plate; causing a test object to impact the trim panel; determining at least one characteristic of the impact; and comparing the characteristic with a reference characteristic.

This system is easier to use because of the kit of inserts that one can use in place of a fixed spring or fluid-type shock absorber. The inserts can be interchanged quickly and easily without any need to set, readjust, or recalibrate.

FIGURES IN THE DRAWINGS

Other advantages of the present invention will be readily appreciated as the same becomes better understood by reference to the following detailed description when considered in connection with the accompanying drawings wherein:

FIG. 1 is a front perspective view of the subject test fixture having a trim panel mounted thereon;

FIG. 2 is a side sectional view of the test fixture taken along line 2—2 in FIG. 1.

DESCRIPTION OF THE PREFERRED EMBODIMENT

Figure 3:
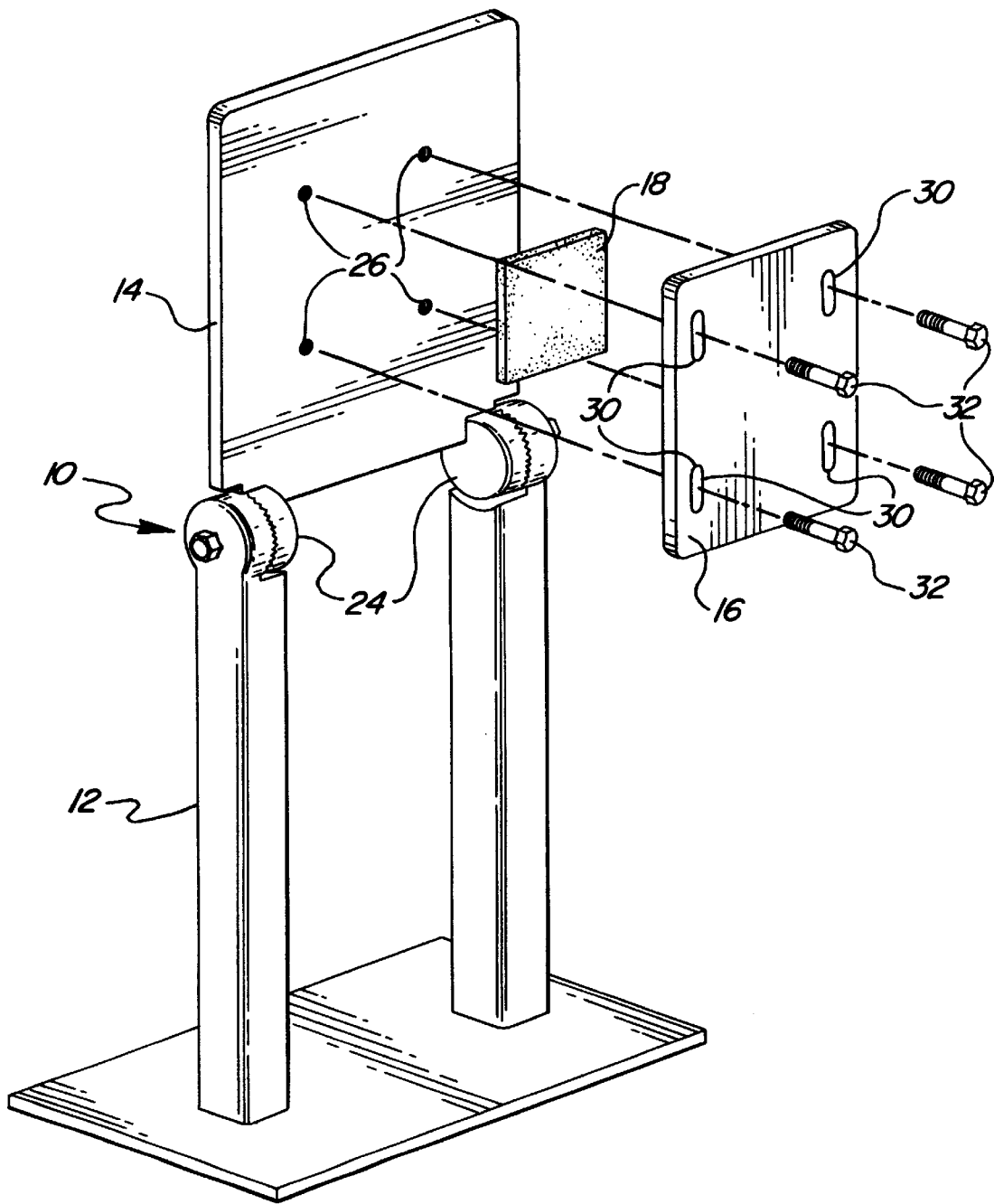
FIG. 3 is an exploded perspective view of the subject test fixture.

Referring to the Figures wherein like numerals indicate like or corresponding parts throughout the several views, an adjustable impact testing fixture is generally shown at 10.

The adjustable fixture 10 comprises a support 12, a backing plate 14 attached to the support, and a movable floating plate 16 supported in spaced-apart relation to the backing plate. One or more energy absorbing inserts 18 are removably disposed between the backing plate 14 and the floating plate 16. The insert 18 causes the fixture to have a predetermined or known impact criteria value. The fixture further includes a mounting assembly 20 adapted to fixedly secure a trim panel 22 to the fixture.

The fixture 10 is typically used for testing head impact criteria (HIC) to determine whether a given interior trim component—when assembled in place in a given vehicle—will meet certain established standards for HIC values. As is known in the art, head impact criteria are typically determined by measuring time and deceleration of the head of a crash dummy as it impacts the fixture. The United States government, for example, has established certain HIC value maximums in order to prevent or reduce serious injuries in actual vehicle crashes. The fixture 10 simulates the steel portion of the vehicle before any trim components are added.

As mentioned, the fixture 10 includes a support 12. The support 12 can be any one of a number of forms, shapes or arrangements. The support preferably attaches to an even larger support structure such as a floor, wall, ceiling, beam, etc. In the embodiment shown in the FIGS., the support 12 is a pair of legs that can attach to a base or a floor.

The fixture further includes a pivot mechanism 24 interconnecting the backing plate 14 and the support 12. A suitable pivot mechanism 24 is illustrated in FIGS. 1 and 3. It allows one to adjust the angular orientation of the parts 14 and 16 vis-à-vis the support 12, and then to fix the angular orientation for a given test. This can simulate impact situations where the impact is with an angled surface—i.e. one that is not perpendicular to the direction of the impact.

The backing plate 14 connects to the pivot mechanism 24. The backing plate 14 is generally a large rectangular piece of metal having holes tapped in the locations shown in the FIGS. This allows the floating plate 16 to be secured to the backing plate.

The floating plate 16 is made from a light-weight, rigid material such as aluminum. As shown in the FIGS, the floating plate 16 is generally smaller in its dimensions than the backing plate 14. A thickness of ¼ inch works well in practice. The floating plate 16 is formed or machined to have four slots 30 as shown to receive the fasteners 32. The fasteners 32 are typically the partially threaded bolts shown best in FIGS. 2 and 3. This arrangement of the slots and fasteners allows the floating plate 16 to float in directions both parallel and perpendicular to the backing plate 14. This is important because an actual impact may not necessarily be perpendicular to the floating plate 16. If the floating plate 16 could not float parallel to the backing plate 14, this would adversely affect the HIC determination—particularly when the impact is not perpendicular to the floating plate 16.

The inserts 18 for the present fixture 10 are preferably a polyurethane foam. However, various materials can be used as the inserts 18. In the preferred case, the material is a rigid or semi-rigid polyurethane foam, and specifically a foam manufactured by the Textron Automotive Company under the designation EM 1080 Series and 1090 Series. The foam is ideally a flat square wave energy management foam like in U.S. Pat. No. 5,232,957. However, even these foams do not give a flat square wave outside of 10–70% compression.

It is important to simulate the variety of surfaces that exist in the vehicle interior. Some are pliant; some are much less so. Theoretically, a single type of foam could be used to get a wide range of HIC values for this kind of simulation. One could simply vary the area of the foam. However, as a practical matter, there are upper and lower limits on the area of foam that can be used. Too small of an area cuts the precision; and too large of an area drives one to use too large and heavy of a floating plate 16. The weight of the plate 16 should be minimized, or accelerating it becomes a significant portion of the HIC value. Also, large foam areas can lead to elastic deformation of the floating plate 16. It is possible that one could construct a floating plate 16 with a larger area that is light enough and stiff enough to permit using one type of foam to cover all the desirable HIC values, but changing the type of foam is easier.

Thus, one can create a "kit" of inserts 18 that—when inserted individually in the fixture 10—will produce a desired range of HIC values. The range can be created by varying the area and compressive strength (i.e. the energy absorbing characteristics) of foam used. The compressive strength will vary not only with the density of the foam, but also with the type of material used to make the foam. Similarly, one could use energy absorbing materials other than foams. One would need to test the materials empirically, or otherwise determine—perhaps mathematically—the HIC characteristics that each piece of foam or material will produce in the fixture 10.

To install the inserts 18, one should remove the floating plate 16 at least partially—i.e., thread it away from the backing plate 14 at least partially. Then one can tape or glue the insert 18 to the backing plate 14—although this is merely convenient and not necessary. Then the bolts 32 are tightened so that the floating plate 16 and the backing plate 14 compress the insert 18 slightly. It is important to compress the foam—especially the aforementioned preferred foam—at least ten percent. This puts the foam into the flat portion of the crush (10–70%) as referenced in U.S. Pat. No. 5,232,957. For example, if the insert 18 is normally 1½ inches thick, the two plates 14, 16 can be adjusted to sandwich the insert 18 to a compressed thickness of 1¼ to 1⅜ inches. This also has the effect of preventing the floating plate 16 from moving very much. The floating plate 16 is always set up parallel to the backing plate 14. One can ensure parallelism simply by using a gauge block to check the clearances between the plates 14, 16 on all sides.

As mentioned, the test fixture 10 further includes a mounting assembly 20 disposed on the floating plate 16 for mounting the test piece of trim 22. The mounting assembly 20 can take many forms. In one version, the mounting assembly 20 is a plurality of spring clips that clip the trim piece 22 onto the floating plate 16.

There is also a corresponding inventive method for simulating the impact characteristics of a given portion of a vehicle—i.e. trim panel 22—with the fixture 10. The method includes the following steps. First is determining the impact characteristics associated with a given energy absorbing insert 18. Next is the step of inserting the insert 18 between a support such as the backing plate 14 and the floating plate such as 16. The backing plate 14 as shown is not strictly necessary. One could mount the floating plate 16 on some other support. In any case, the plates 14, 16 and the insert 18 should produce an impact result equivalent to a given untrimmed impact point of interest in the vehicle.

The next step involves mounting a vehicle trim panel 22 on the floating plate 16. After that, one causes a test object to impact the trim panel 22. Then one determines at least one characteristic of the impact, and compares the characteristic with a reference characteristic. It is expected that adding the trim panel 22 will produce a lower impact characteristic (e.g. HIC value) than the value expected with just the insert 18 and the plates 14, 16. Whether this lower value conforms to a given requirement is of course the point of the test.

Prior to performing the first step, one must know the impact characteristics of various features of the inside of a vehicle—the features that one is trying to simulate with the fixture. These features are the untrimmed steel and sheet metal portions of the vehicle frame such as the "A" and "B" pillars, and the roof rails. One can either perform one's own tests, and "map" the impact (e.g. HIC) characteristics of these features, or rely on such a map created by someone else. One can expect that these impact values will be high and out of conformance with both the federal requirements and the vehicle manufacturer's internal requirements at each given impact point. Also, one can expect the impact values to vary from point to point.

The first step of analyzing the insert 18 can be performed—at least initially—empirically or possibly mathematically. For example, one can test the head impact criteria produced with the fixture 10 by a given insert 18 with a series of tests to provide a statistically accurate determination.

Once the criteria are determined initially for a variety of samples, a person could construct a table or chart for future determination. This table could allow a person to quickly determine which insert 18 to put in the fixture 10 to simulate the HIC characteristics of a given portion of the vehicle.

Next, the fixture 10 is assembled with the insert 18 disposed between the support 12, for example, and the floating plate 16, for example, to simulate a given portion of the vehicle. An example of this set-up is described above in detail. The final part of the fixture set-up involves mounting the test piece of trim 22 on the floating plate 16 as shown in the FIGS. This final assembly simulates a portion of a vehicle for purposes of the impact testing.

From here, one can test the impact characteristics of the trim panel 22 according to known techniques. In one case, this involves crashing a crash dummy head—or "free motion headform (FMH)"—into the trim panel 22.

The crash dummy head has three accelerometers in it to measure acceleration or deceleration of the dummy head as it impacts the trim panel 22. Each accelerometer measures acceleration in a single plane. Since the headform is "free," one needs to measure in all three planes. From the three acceleration values ($A_x$, $A_y$, $A_z$) a "resultant" is calculated: $A_R$=the square root of $A_x^2 + A_y^2 + A_z^2$.

One should also have a computer data acquisition system for measuring the time of the head motion and deceleration event, specifically the time of deceleration. The desired output of the measurements is a resultant acceleration vs. time plot. The resultant acceleration is the resultant vector from the acceleration in each of the three directions, calculated by the known formula:

$$A_R = (A_X^2 + A_Y^2 + A_Z^2)^{1/2}$$

This data is then integrated in a computer to give a HIC value according to the known formula:

$$HIC = \left[\left(\frac{1}{t_2 - t_1}\right) \int_{t_1}^{t_2} A_R \, dt\right]^{2.5}_{t_2 - t_1}$$

HIC is calculated using the acceleration readings from the instrumented free motion headform (FMH), and transforming it into a dummy equivalent HIC(d). This represents the HIC that would be experienced by a full dummy or actual vehicle occupant. Again, this is done according to a known formula:

$$H.I.C.(d) = 0.75446(H.I.C.) + 166.4$$

The result is the final output of the whole test. In this case it measures the head impact criteria that a full dummy would experience if it crashed into the fixture 10 with the given insert 18 and with the given trim panel 22 mounted on the floating plate 16. This result is then compared against some standard. According to the U.S. government, the standard for HIC(d) is 1000. Many vehicle manufacturers use a lower number such as 800—which is actually a higher safety standard—in order to ensure a margin of safety. If the tested trim panel 22 has a HIC(d) exceeding the given standard, it is rejected; if it has a lower HIC(d), it passes.

The invention has been described in an illustrative manner, and it is to be understood that the terminology which has been used is intended to be in the nature of words of description rather than of limitation.

Obviously, many modifications and variations of the present invention are possible in light of the above teachings. Therefore, it is to be understood that within the scope of the appended claims the invention may be practiced otherwise than as specifically described. Moreover, the reference numerals are merely for convenience and are not intended to be in any way limiting.

We claim:

1. An adjustable fixture for impact testing of vehicle interior trim panels, said adjustable fixture comprising:
    a support;
    a backing plate attached to said support;
    a movable floating plate supported in spaced apart relation to said backing plate;
    an energy absorbing insert removably disposed between said backing plate and said floating plate; and
    a mounting assembly adapted to fixedly secure a trim panel to said floating plate;
    said insert causing said fixture to have a predetermined impact characteristic.

2. The adjustable fixture of claim 1 wherein said insert is a foam.

3. The adjustable fixture of claim 2 wherein said insert is a plastic foam.

4. The adjustable fixture of claim 3 wherein said insert is a thermoset foam.

5. The adjustable fixture of claim 4 wherein said insert is polyurethane foam.

6. The adjustable fixture of claim 1 wherein said floating plate and said backing plate compress said insert slightly.

7. The adjustable fixture of claim 1 wherein said floating plate defines a plurality of slots; said fixture further including a plurality of fasteners extending through said slots and fastening to said backing plate.

8. The adjustable fixture of claim 1 further including a pivot mechanism interconnecting said backing plate and said support.

9. The adjustable fixture of claim 1 wherein said characteristic is a head impact criteria.

10. An adjustable fixture for impact testing of vehicle interior trim panels, said adjustable fixture comprising:
    a support;
    a backing plate attached to said support;
    a movable floating plate supported in spaced apart relation to said backing plate;
    a plurality of energy absorbing inserts removably disposable, one at a time, between said backing plate and said floating plate; and
    a mounting assembly adapted to fixedly secure a trim panel to said fixture;
    said inserts each causing said fixture to have a predetermined impact characteristic.

11. A method for simulating the impact characteristics of a given portion of a vehicle with a fixture having a support and a floating plate supported on the support, the method including the steps of:
    determining an impact characteristic associated with a given energy absorbing insert;
    inserting the insert between the support and the floating plate;
    mounting a vehicle trim panel on the floating plate;
    causing a test object to impact the trim panel;
    determining at least one characteristic of the impact; and
    comparing the characteristic with a reference characteristic.

* * * * *